(12) United States Patent
Ono et al.

(10) Patent No.: US 11,331,454 B2
(45) Date of Patent: May 17, 2022

(54) NEEDLE TIP PROTECTOR FOR INDWELLING NEEDLE AND INDWELLING NEEDLE ASSEMBLY

(71) Applicant: NIPRO CORPORATION, Osaka (JP)

(72) Inventors: Yoshiei Ono, Osaka (JP); Kohzo Ishikura, Osaka (JP); Tatsuya Kudo, Osaka (JP); Takeshi Yamaguchi, Osaka (JP)

(73) Assignee: NIPRO CORPORATION, Osaka (JP)

( * ) Notice: Subject to any disclaimer, the term of this patent is extended or adjusted under 35 U.S.C. 154(b) by 738 days.

(21) Appl. No.: 16/306,624

(22) PCT Filed: Jun. 2, 2017

(86) PCT No.: PCT/JP2017/020720
§ 371 (c)(1),
(2) Date: Dec. 3, 2018

(87) PCT Pub. No.: WO2017/209304
PCT Pub. Date: Jul. 12, 2017

(65) Prior Publication Data
US 2019/0160265 A1    May 30, 2019

(30) Foreign Application Priority Data
Jun. 3, 2016   (JP) .............................. JP2016-112071

(51) Int. Cl.
*A61M 25/06*   (2006.01)
*A61M 5/158*   (2006.01)
*A61M 5/32*    (2006.01)

(52) U.S. Cl.
CPC ........ *A61M 25/0637* (2013.01); *A61M 5/158* (2013.01); *A61M 5/3271* (2013.01);
(Continued)

(58) Field of Classification Search
CPC .............. A61M 5/158; A61M 25/0637; A61M 25/0631; A61M 2005/1587; A61M 2005/3247
See application file for complete search history.

(56) References Cited

U.S. PATENT DOCUMENTS

2004/0236287 A1   11/2004   Swenson et al.
2007/0260190 A1*  11/2007   Lin .................. A61M 25/0637
                                                       604/192

FOREIGN PATENT DOCUMENTS

EP    0664139 A1    7/1995
EP    0830871 A2    3/1998
(Continued)

OTHER PUBLICATIONS

English translation of the International Preliminary Report on Patentability (Chapter I) issued in International Application No. PCT/JP2017/020720, dated Dec. 13, 2018, 7 pages.
(Continued)

*Primary Examiner* — Tiffany Legette
(74) *Attorney, Agent, or Firm* — Edell, Shapiro & Finnan, LLC

(57) ABSTRACT

The present invention provides a needle tip protector of a novel structure for an indwelling needle, which enables improvements in safety, etc. as compared with conventional needle tip protectors. A needle tip protector 10 for an indwelling needle includes a tubular peripheral wall 58, and is externally attached over a needle hub 22 of an indwelling needle 16 and moved toward a needle tip 14 side so as to cover the needle tip 14. Detents 74, 74, which are to be detained with the needle hub 22 at a position in a movement of the protector toward the needle tip 14 side of the indwelling needle 16 so as to inhibit backward movement of the protector to the proximal end side of the indwelling needle 16 and to prevent the needle tip 14 from being reexposed, are
(Continued)

formed within an inside enclosed by the peripheral wall 58, and are integrally molded with the peripheral wall 58.

15 Claims, 7 Drawing Sheets

(52) U.S. Cl.
 CPC . *A61M 25/0631* (2013.01); *A61M 2005/1587* (2013.01); *A61M 2005/3247* (2013.01)

(56) References Cited

FOREIGN PATENT DOCUMENTS

| | | | |
|---|---|---|---|
| EP | 2578250 | A1 | 4/2013 |
| JP | H7204267 | A | 8/1995 |
| JP | H1085333 | A | 4/1998 |
| JP | 3134920 | B2 | 2/2001 |
| JP | 2002345955 | A | 12/2002 |
| JP | 2004223252 | A | 8/2004 |
| JP | 2004275741 | A | 10/2004 |
| JP | 2008-29812 | A | 2/2008 |
| JP | 2008029812 | A | 2/2008 |
| JP | 2013-192738 | A | 9/2013 |

OTHER PUBLICATIONS

International Search Report for International Application No. PCT/JP2017/020720 dated Aug. 1, 2017, 5 pages.
First Office Action issued in Indian Patent Application No. 201817045346 dated Jun. 29, 2021 with English translation, 7 pages.
Extended European Search Report received in European App. No. 20193695.2, dated Sep. 30, 2020 (6 pages).
First Office Action issued in Japanese Patent Application No. 2018-521150, dated Jan. 26, 2021 (9 pages).
Extended European Search Report in corresponding EP Application No. 17806854.0, dated Feb. 11, 2019, 7 pages.
First Office Action issued in Japanese Patent Application No. 2020-007087, dated Oct. 27, 2020 (7 pages).
First Office Action issued in Chinese Patent Application No. 201780034358.8, dated Oct. 23, 2020 (17 pages).

* cited by examiner

NEEDLE TIP PROTECTOR FOR INDWELLING NEEDLE AND INDWELLING NEEDLE ASSEMBLY

CROSS REFERENCE TO RELATED APPLICATIONS

This application is 371 National Stage of International Application No. PCT/JP2017/020720, filed on Jun. 2, 2017, and claims priority under 35 U.S.C. § 119 to Application No. JP 2016-112071, filed on Jun. 3, 2016, the contents of which are incorporated by reference herein in their entirety.

TECHNICAL FIELD

The present invention relates to a needle tip protector for an indwelling needle in order to protect a needle tip of an indwelling needle after use of the indwelling needle that punctures a blood vessel and is placed therein, and an indwelling needle assembly including a needle tip protector.

BACKGROUND ART

Conventionally, indwelling needles used for infusion, blood collection, and hemodialysis are known. This indwelling needle has a needle tip at its distal end, while its proximal end is fixed to a needle hub. Infusion, blood collection, and hemodialysis are carried out through an external conduit such as a cannula connected to the needle hub by puncturing the patient's blood vessel with the indwelling needle and placing the needle therein.

Meanwhile, some indwelling needles have a needle tip protector for protecting the needle tip after use, for the purpose of preventing erroneous puncture or reuse, or facilitating disposal processing. For example, Japanese Patent No. JP-B-3134920 (Patent Document 1) proposed by the present applicant discloses a needle tip protector for such an indwelling needle and an indwelling needle assembly having a needle tip protector.

That is, the needle tip protector described in Patent Document 1 has a tubular peripheral wall, and after the indwelling needle is used, by moving the peripheral wall to the needle tip side, the needle tip of the indwelling needle is configured to be protected by the needle tip protector. Specifically, before use of the indwelling needle, the needle tip protector and the needle hub are coupled and fixed in a state in which the needle tip of the indwelling needle is exposed, but after use the coupling between the needle tip protector and the needle hub is released, such that the needle tip protector moves to the needle tip side with respect to the needle hub thereby protecting the needle tip and holding the state with a detent (flexible abutment branch 43). Adopting such a needle tip protector and an indwelling needle assembly makes it possible to safely protect the needle tip of the indwelling needle and effectively prevent the possibility of erroneous puncture or the like.

The applicant of the present application has examined further improvements of such a needle tip protector and an indwelling needle assembly, and was able to develop the present invention that is superior to the needle tip protector and the indwelling needle assembly described in Patent Document 1 in safety or the like.

BACKGROUND ART DOCUMENT

Patent Document

Patent Document 1: JP-B-3134920

SUMMARY OF THE INVENTION

Problem the Invention Attempts to Solve

The present invention has been made in view of the above circumstances, and it is an object of the present invention to provide a needle tip protector for an indwelling needle and an indwelling needle assembly of a novel structure capable of improving safety or the like, as compared with the background art.

Means for Solving the Problem

The above and/or optional objects of this invention may be attained according to at least one of the following modes of the invention. The following modes and/or elements employed in each mode of the invention may be adopted at any possible optional combinations.

A first mode of the present invention provides a needle tip protector for an indwelling needle including a tubular peripheral wall and configured to cover a needle tip of the indwelling needle by being externally mounted about a needle hub of the indwelling needle and by being moved to a needle tip side, the needle tip protector being characterized in that at least one detent is formed in an inside covered with the tubular peripheral wall and is configured to be detained with the needle hub at a position in a movement of the protector to the needle tip side of the indwelling needle and to prevent backward movement of the protector to a proximal end side of the indwelling needle such that reexposure of the needle tip is prevented, and the detent is integrally molded with the tubular peripheral wall.

According to the needle tip protector structured following this mode, since the detent for preventing the needle tip from being reexposed is integrally formed inside the peripheral wall, it is possible to make it difficult to access the detent from the outside. As a result, it is also possible to prevent unintentional contact with the detent or breakage of the detent due to some external force that may cause release of the protected state of the needle tip or the like.

A second mode of the present invention provides the needle tip protector according to the first mode, wherein the detent extends within the tubular peripheral wall toward a proximal end side of the peripheral wall.

According to the needle tip protector structured following this mode, the detent extends toward the proximal end side of the peripheral wall. Thus, when the indwelling needle is moved toward the proximal end side with respect to the needle tip protector, it is possible to reduce the possibility of catching or a resistance feeling by the user, compared with, for example, the case where the detent extends to the distal end side.

A third mode of the present invention provides the needle tip protector according to the first or second mode, wherein the detent is entirely housed in the inside covered with the tubular peripheral wall.

According to the needle tip protector structured following this mode, since the entire detent is housed inside the peripheral wall, access from the outside to the detent is more difficult. This will more effectively prevent the needle tip from being unexpectedly exposed, and further improvement of safety can be achieved.

A fourth mode of the present invention provides the needle tip protector according to any one of the first to third modes, wherein an expansion part expanding radially outward is provided to a proximal end side of the tubular peripheral wall, and the detent is provided in the expansion part.

According to the needle tip protector structured following this mode, since the detent is provided in the expansion part provided on the proximal end side of the peripheral wall, the size of the detent is sufficiently ensured, while preventing the diameter of the needle hub inserted into the peripheral wall from becoming too small.

A fifth mode of the present invention provides the needle tip needle protector according to the fourth mode, wherein a stepped surface is provided to a front end portion of the expansion part, the stepped surface facing forward and extending radially outward on a radially inner surface of the tubular peripheral wall, and the detent protrudes backward from a more backward end portion of the expansion part than the stepped surface.

According to the needle tip protector structured following this mode, the stepped surface facing forward and extending radially outward is provided on the radially inner surface of the peripheral wall. Thus, for example, by providing a detent projection protruding radially outward on the outer peripheral surface of the needle hub, when the indwelling needle is moved toward the proximal end side with respect to the needle tip protector, the detent projection and the stepped surface are engaged with each other, thereby limiting further movement of the indwelling needle to the proximal end side. Therefore, it is also possible to prevent the indwelling needle from falling out from the proximal end side of the needle tip protector by using the detent.

A sixth mode of the present invention provides the needle tip protector according to the fourth or fifth mode, wherein the expansion part has a roughly oval tube shape including a small-diameter part and a large-diameter part that are orthogonal to each other, the detent is provided in an inside covered with a peripheral wall of the large-diameter part, and the peripheral wall of the large-diameter part includes a needle hub engager configured to receive the needle hub such that the needle tip of the indwelling needle is held in a protruding state.

According to the needle tip protector structured following this mode, since the expansion part is formed in a roughly oval tube shape having no corner, the risk of the expansion part contacting the patient to cause the patient to feel pain may be reduced. Particularly, since the expansion part has the small-diameter part, the amount of contact with the patient can be decreased, and the risk that the patient feels pain can be further reduced.

Further, instead of merely providing a thick-walled large-diameter part, by providing a detent inside the large-diameter part, it is possible to utilize the internal space of the expansion part successfully and to prevent mixing of the air to the components effectively, whereby the quality of the product can be improved, namely, the dimensional error can be reduced or the like.

A seventh mode of the present invention provides the needle tip protector according to any one of the first to sixth modes, wherein the at least one detent comprises a plurality of detents that are remote from each other in a circumferential direction of the tubular peripheral wall.

According to the needle tip protector structured following this mode, since a plurality of detents are provided so as to be remote from each other in the circumferential direction, backward movement of the protector toward the proximal end side of the indwelling needle can be more reliably prevented. Thus, the effect of preventing reexposure of the needle tip can be exhibited more stably.

An eighth mode of the present invention provides the needle tip protector according to any one of the first to seventh modes, wherein a free end side of the detent extending from the tubular peripheral wall comprises a first detent configured to be detained with the needle hub such that reexposure of the needle tip due to movement of the indwelling needle to the needle tip side in the tubular peripheral wall is prevented, and a fixed end side of the detent integrally supported by the tubular peripheral wall comprises a second detent configured to be detained with the needle hub such that needle dislodgment due to movement of the indwelling needle to the proximal end side is prevented.

According to the needle tip protector structured following this mode, movement of the indwelling needle in both directions toward the distal end side and the proximal end side with respect to the needle tip protector is prevented by the detent formed on the peripheral wall. Thus, the structure can be simplified as compared with the case where the needle tip reexposure prevention mechanism and the needle dislodgment prevention mechanism are separately provided.

A ninth mode of the present invention provides the needle tip protector according to any one of the first to eighth modes, wherein a deformation amount limiter configured to limit an amount of deformation of the detent to a radially outer side is provided.

According to the needle tip protector structured following this mode, in a state in which the detent moves to the needle tip side of the indwelling needle and is detained with the needle hub, even when an external force such as the one in the bending direction is exerted on the needle tip protector and/or the needle hub, for example, deformation of the detent to the radially outer side is restricted by the deformation amount limiter. This will reduce the risk of release of the detainment of the detent with respect to the needle hub, and the protected state of the needle tip of the indwelling needle can be stably maintained.

A tenth mode of the present invention provides an indwelling needle assembly including the needle tip protector according to any one of the first to ninth modes, and an indwelling needle having a needle hub at a proximal end side thereof, the indwelling needle being inserted in the needle tip protector such that the indwelling needle is movable in an axial direction, wherein the detent provided to the needle tip protector is configured to be detained with the needle hub at a predetermined position where the protector is moved to the needle tip side of the indwelling needle such that reexposure of the needle tip of the indwelling needle is prevented.

According to this mode, it is possible to provide an indwelling needle assembly by which the working effects as described in any one of the first to ninth modes are exhibited and the needle tip of the indwelling needle is prevented from being reexposed.

An eleventh mode of the present invention provides the indwelling needle assembly according to the tenth mode, wherein a free end side of the detent extending from the tubular peripheral wall comprises a first detent configured to be detained with the needle hub such that reexposure of the needle tip due to movement of the indwelling needle to the needle tip side in the tubular peripheral wall is prevented, a fixed end side of the detent integrally supported by the tubular peripheral wall comprises a second detent configured to be detained with the needle hub such that needle dislodgment due to movement of the indwelling needle to the proximal end side is prevented, and the needle hub includes a detaining recess, and an inner surface on a proximal end side of the detaining recess comprises a third detent with which the first detent configured to be detained.

According to the indwelling needle assembly structured following this mode, since the first detent and the second detent of the detent of the needle tip protector are detained with the needle hub, the indwelling needle is prevented from moving in both directions toward the distal end side and the proximal end side with respect to the needle tip protector. Thus, the structure can be simplified or compact as compared with the case where the needle tip reexposure prevention mechanism and the needle dislodgment prevention mechanism are separately provided.

A twelfth mode of the present invention provides the indwelling needle assembly according to the tenth or eleventh mode, wherein a free end side of the detent extending from the tubular peripheral wall comprises a first detent, and the first detent is configured to be detained with a third detent provided on an outer circumferential surface of the needle hub such that reexposure of the needle tip due to movement of the indwelling needle to the needle tip side in the tubular peripheral wall is prevented, a proximal end face of the first detent includes a first axis-perpendicular face that crosses orthogonally to a needle axis direction of the indwelling needle, and the third detent includes a third axis-perpendicular face that crosses orthogonally to the needle axis direction of the indwelling needle.

According to the indwelling needle assembly structured following this mode, the mutual abutting surfaces of the first detent and the third detent comprise the first axis-perpendicular face and the third axis-perpendicular face spreading orthogonally to the direction of abutment. Thus, it is possible to realize a detent that exhibits a greater movement prevention force without adopting the undercut shape which is likely to be difficult to mold.

A thirteenth mode of the present invention provides the indwelling needle assembly according to the twelfth mode, wherein an end of the first axis-perpendicular face of the first detent, the end being on a radially outer side of the needle tip protector, is positioned on a radially inner side than an end of the third axis-perpendicular face provided to the needle hub, the end being on a radially outer side of the needle hub.

According to the indwelling needle assembly structured following this mode, even when the first detent is slightly deformed by the abutment between the first detent and the third detent to cause the first axis-perpendicular face to be inclined, the end of the first axis-perpendicular face on the radially outer side is located on the third axis-perpendicular face, so that the occurrence of the component force in the direction in which the first detent rides over the third detent is suppressed, thereby realizing more stable detained state.

Effect of the Invention

According to the needle tip protector for an indwelling needle structured following the present invention, since the detent for preventing the needle tip from being reexposed is integrally formed inside the peripheral wall, unintended contact with the detent or the like can be avoided, thereby improving safety.

EMBODIMENTS FOR CARRYING OUT THE INVENTION

Figure 1:
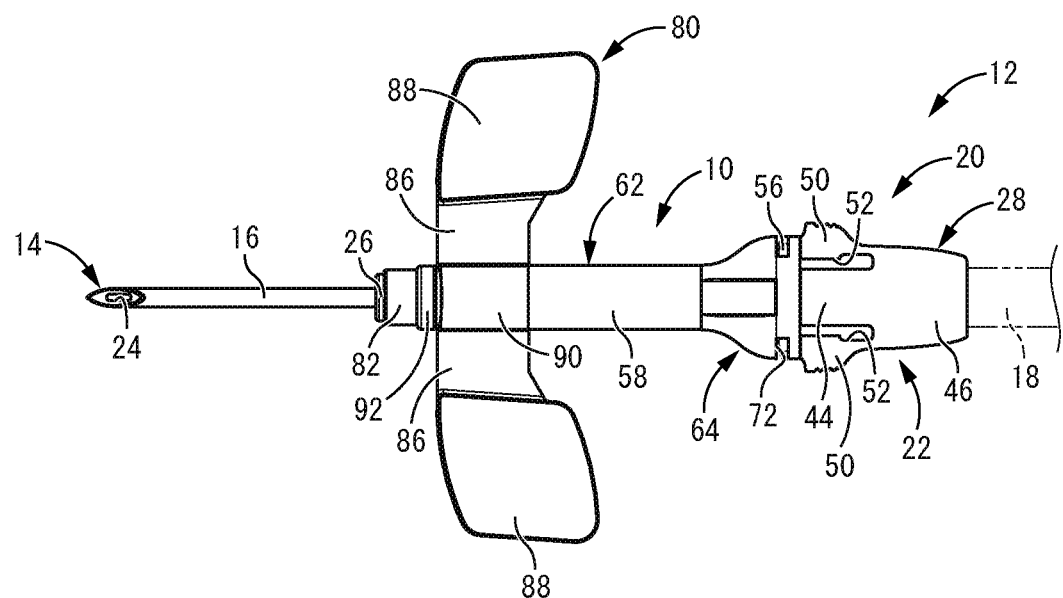
FIG. 1 is a plan view showing an indwelling needle assembly including a needle tip protector for an indwelling needle according to a first embodiment of the present invention with a needle tip extended.
Figure 2:
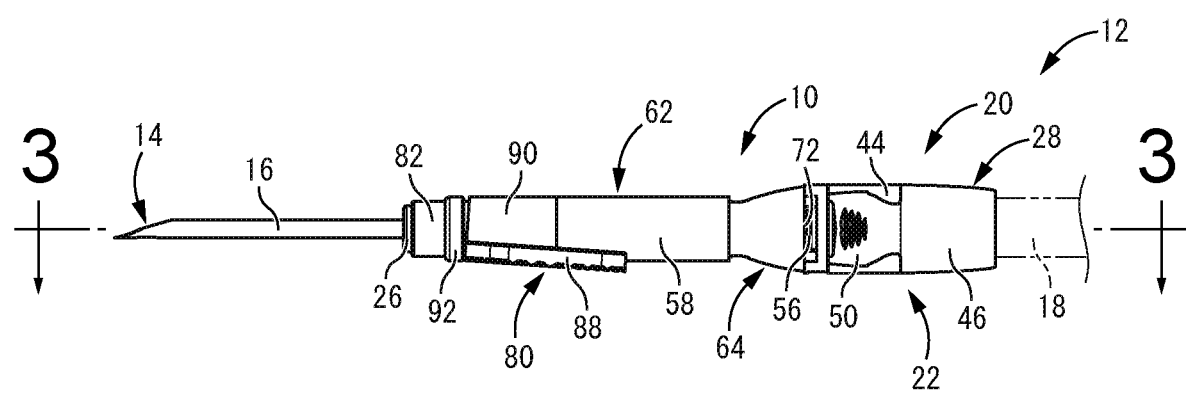
FIG. 2 is a front view of the indwelling needle assembly shown in FIG. 1.
Figure 3:
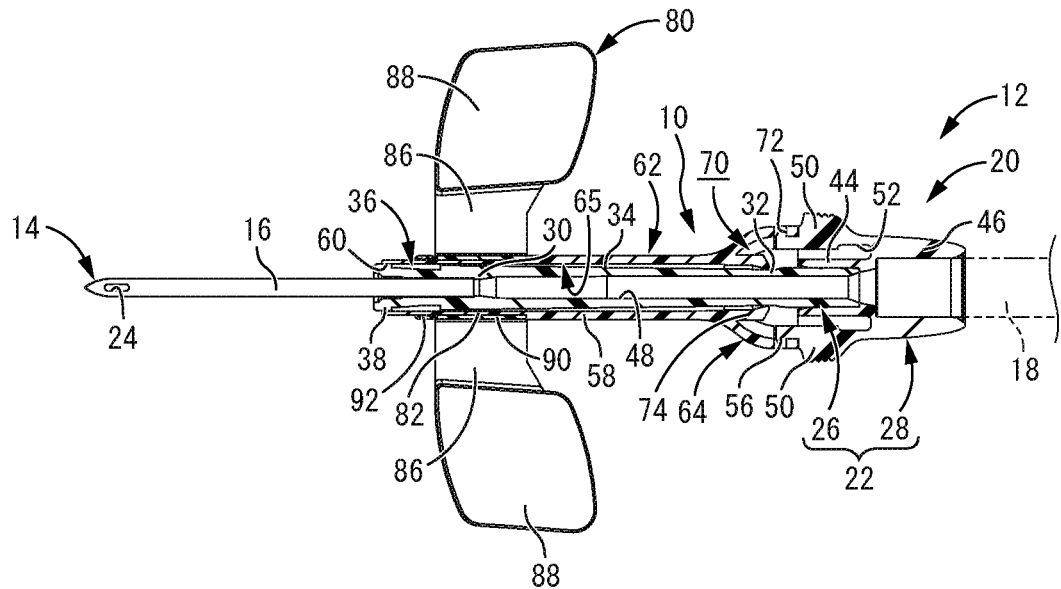
FIG. 3 is a cross sectional view taken along line 3-3 of FIG. 2.
Figure 4:
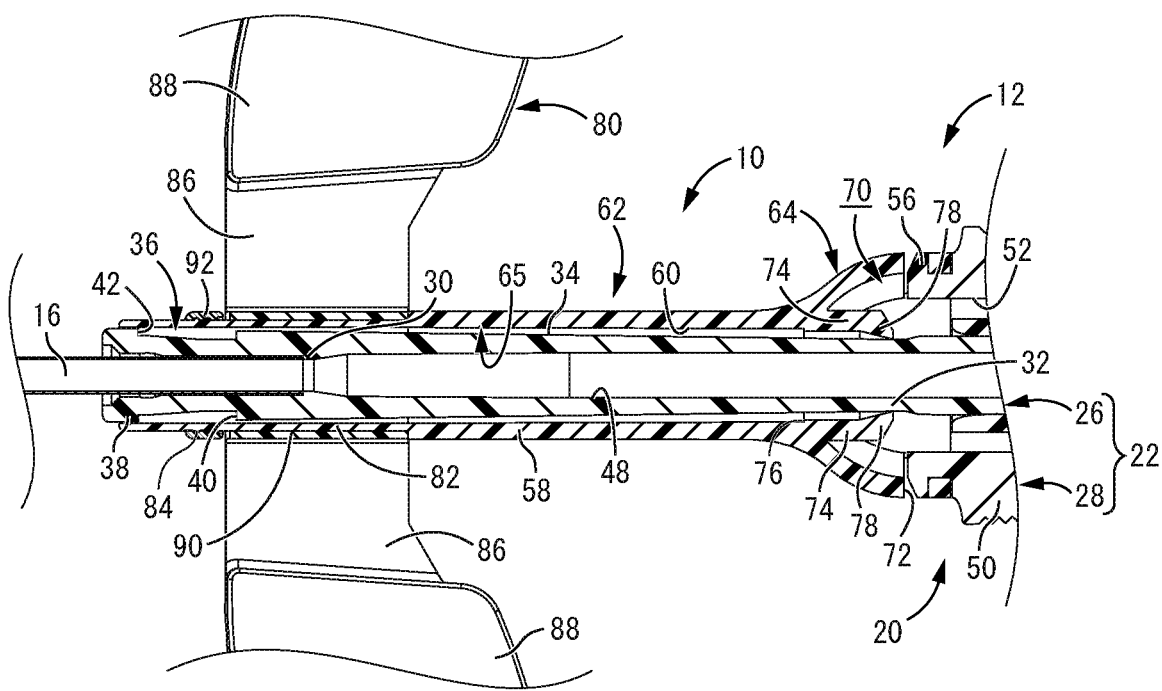
FIG. 4 is an enlarged cross sectional view of a principal part in FIG. 3.

Hereinafter, embodiments of the present invention will be described with reference to the drawings.

First, FIGS. 1 to 4 show an indwelling needle assembly 12 including a needle tip protector 10 for an indwelling needle according to a first embodiment of the present invention. The indwelling needle assembly 12 includes an indwelling needle 16 having a needle tip 14 and a needle tip protector 10 through which the indwelling needle 16 is movably inserted in the needle axis direction. By the indwelling needle 16 being stuck into a patient's blood vessel and placed therein, infusion, blood collection, hemodialysis and the like are performed through an external conduit 18 such as a cannula or the like connected to the proximal end side of the indwelling needle assembly 12. After use of the indwelling needle 16, the indwelling needle 16 is removed from the blood vessel of the patient, and the needle tip protector 10 is moved toward the needle tip 14 side so that the needle tip 14 of the indwelling needle 16 is covered and protected by the needle tip protector 10. In the following description, the distal end side or the front side refers to the left side in FIG. 1, which is the needle tip 14 side of the indwelling needle 16, whereas the proximal end side or the back side refers to the right side in FIG. 1, which coincides with the back side in the puncture direction of the indwelling needle 16.

More specifically, the indwelling needle assembly 12 is configured such that the needle tip protector 10 is externally mounted onto a needle unit 20 including the indwelling needle 16. The needle unit 20 is composed of the indwelling needle 16 and a needle hub 22 for fixedly supporting the proximal end side of the indwelling needle 16.

The indwelling needle 16 is a hollow needle made of metal, for example, and is made of stainless steel or the like. The needle tip 14 of the indwelling needle 16 is tapered and has a sharp shape. A through hole 24 is formed in the needle tip 14 of the indwelling needle 16, and the blood easily flows into the indwelling needle 16.

On the other hand, the needle hub 22 includes a needle hub main body 26 and a support part 28 fixedly supporting the needle hub main body 26, both having a roughly tubular shape. The needle hub main body 26 and the support part 28 are coupled to each other in the needle axis direction of the indwelling needle 16 (lateral direction in FIG. 1).

The needle hub main body 26 is formed in a round tubular shape having a substantially constant inside diameter dimension overall, and is made of, for example, a rigid synthetic resin. The inside diameter dimension of the distal end opening of the needle hub main body 26 is substantially equal to the outside diameter dimension of the indwelling needle 16, while on the radially inner surface of the distal end portion of the needle hub main body 26, an annular positioning protrusion 30 is provided so as to protrude to the radially inner side. The proximal end side of the indwelling needle 16 is inserted from the distal end opening of the needle hub main body 26 so that the proximal end of the indwelling needle 16 and the positioning protrusion 30 are brought into abutment against each other so that the proximal end of the indwelling needle 16 is positioned. Further, as necessary, the needle hub main body 26 and the indwelling needle 16 are bonded to each other so that the indwelling needle 16 is fixedly supported on the distal end of the needle hub main body 26.

On the other hand, the outside diameter dimension of the needle hub main body 26 differs in the needle axis direction. That is, a small-diameter tube part 32 having an outside diameter dimension smaller than that of the proximal end portion is provided in the axially medial portion of the needle hub main body 26. The outer peripheral surface of the needle hub main body 26 further on the distal end side than the small-diameter tube part 32 is a tapered surface 34 whose outside diameter dimension gradually increases toward the distal end side.

Further, on the outer peripheral surface of the needle hub main body 26 further on the distal end side than the tapered surface 34, an annular detaining recess 36 opening radially outward is formed. The detaining recess 36 has a predetermined width dimension (needle axial dimension), and the minimum outside diameter dimension of the needle hub main body 26 at the forming location of the detaining recess 36 is roughly equal to the outside diameter dimension of the small-diameter tube part 32. Furthermore, an annular detaining projection 38 protruding radially outward is formed on the outer peripheral surface further on the distal end side than the detaining recess 36. The outside diameter dimension of the detaining projection 38 is larger than the maximum outside diameter dimension of the distal end portion of the tapered surface 34.

Figure 9:
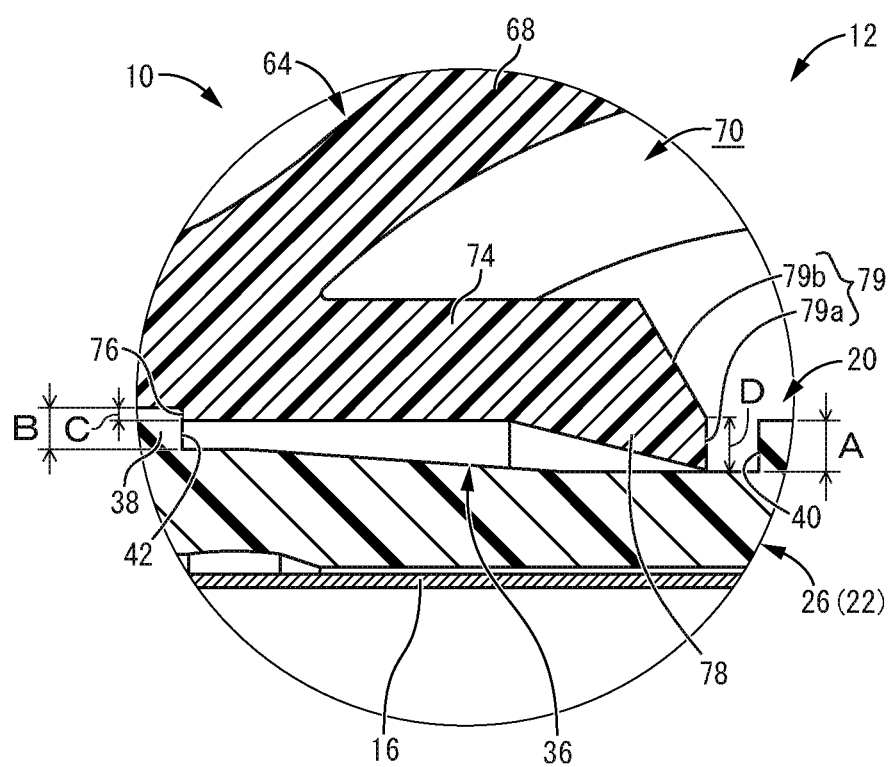
FIG. 9 is a cross sectional view further enlarging the principal part in FIG. 7.

The proximal end side surface constituting the inner surface of the detaining recess 36 is an annular proximal-end-side restricting surface 40 serving as a third detent extending in the axis-perpendicular direction with a predetermined dimension A (see FIG. 9). The bottom surface of the detaining recess 36 and the tapered surface 34 are continuous in a stepped shape owing to the proximal-end-side restricting surface 40. On the other hand, the distal end side surface constituting the inner surface of the detaining recess 36 is an annular distal-end-side restricting surface 42 serving as a fourth detent extending in the axis-perpendicular direction with a predetermined dimension B (see FIG. 9). The bottom surface of the detaining recess 36 and the outer peripheral surface of the detaining projection 38 are continuous in a stepped shape owing to the distal-end-side restricting surface 42. In the present embodiment, the dimension A in the axis-perpendicular direction of the proximal-end-side restricting surface 40 constituted by the inner surface at the proximal end side of the detaining recess 36 is slightly larger than the dimension B in the axis-perpendicular direction of the distal-end-side restricting surface 42.

Further, the support part 28 is formed in a substantially round tubular shape with a step formed on the radially inner surface overall, and is formed of a rigid synthetic resin, for example, similar to the needle hub main body 26. That is, with the support part 28, while the distal end side comprises a coupling tube 44 having a small inside diameter dimension, the proximal end side comprises a connecting tube 46 having a large inside diameter dimension. The proximal end of the needle hub main body 26 is inserted into the coupling tube 44, and the needle hub main body 26 and the support part 28 are coupled to each other by bonding or welding as necessary. On the other hand, the distal end of the external conduit 18 is inserted into the connecting tube 46, and the support part 28 and the external conduit 18 are connected to each other by bonding or welding as necessary. Therefore, the inner holes of the indwelling needle 16 and the needle hub 22 (the needle hub main body 26 and the support part 28) constitute a fluid flow path 48 extending from the blood vessel to the external conduit 18.

A pair of engaging arms 50, 50 protruding to the distal end side with a predetermined width dimension are integrally formed at the outer peripheral edge portion of the connecting tube 46 on both sides in one diametrical direction (both sides in the vertical direction in FIG. 1). The engaging arms 50, 50 are substantially rectangular in plan view, and the plate thickness dimension (vertical dimension in FIG. 1) and the width dimension (vertical dimension in FIG. 2) of the proximal end portion (connected portion with the connecting tube 46) is made thin. Besides, slit-like gaps 52, 52 are formed radially between the coupling tube 44 and the engaging arms 50, 50, so that the engaging arms 50, 50 can be elastically deformed in the plate thickness direction. Also, hooks 56, 56 projecting to the outer peripheral side are formed at the distal end portions of the engaging arms 50, 50.

Figure 5:
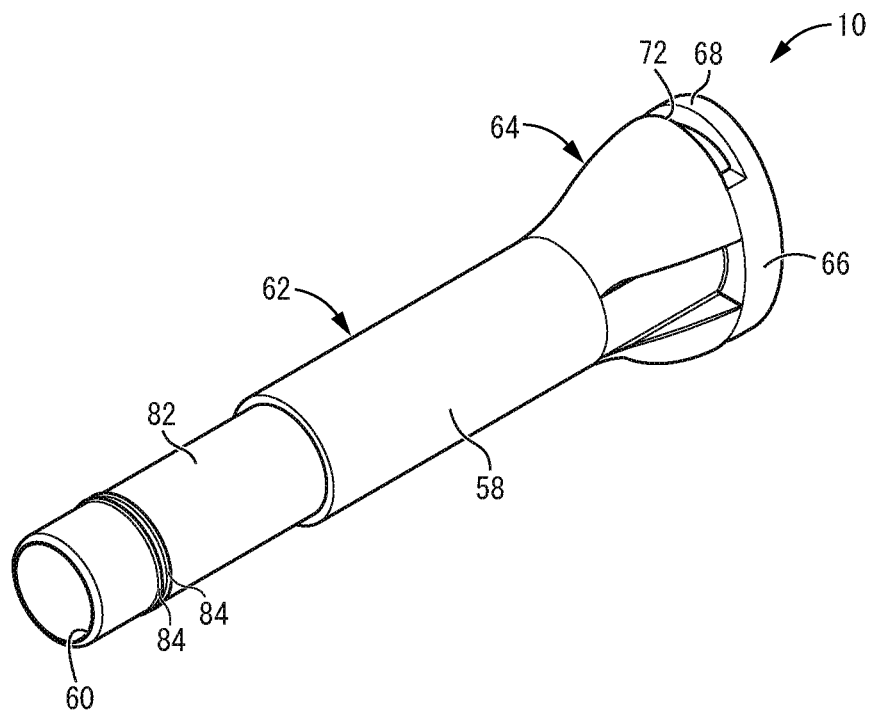
FIG. 5 is an enlarged perspective view showing the needle tip protector for an indwelling needle constituting the indwelling needle assembly shown in FIG. 1.
Figure 6:
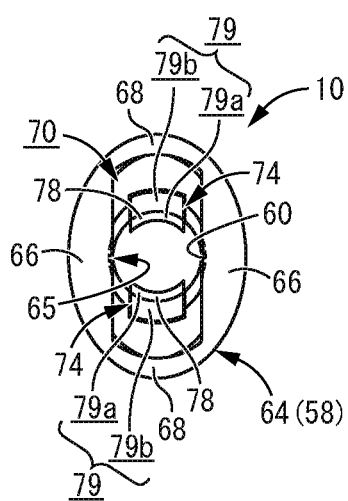
FIG. 6 is a right side view of the needle tip protector for an indwelling needle shown in FIG. 5.

Meanwhile, as shown in FIGS. 5 and 6, the needle tip protector 10 has a substantially tubular shape extending in the needle axis direction overall, and is integrally formed of a rigid synthetic resin such as polypropylene, polycarbonate, polyethylene terephthalate glycol, or ABS resin. That is, the needle tip protector 10 includes a tubular peripheral wall 58 and an inner hole 60 penetrating the interior of the peripheral wall 58 in the needle axis direction.

The needle tip protector 10 (peripheral wall 58) has a shape that differs in the needle axis direction, namely, the distal end side comprises a cylindrical portion 62 whose cross section is formed into a substantially perfect circular ring shape, and the proximal end side comprises an expanded part 64 serving as an expansion part having a diameter larger than that of the cylindrical portion 62 and expanding radially outward. That is, the peripheral wall 58 of the needle tip protector 10 includes the peripheral wall of the cylindrical portion 62 and the peripheral wall of the expanded part 64, while a radially inner surface 65 of the peripheral wall 58 includes the radially inner surface of the peripheral wall of the cylindrical portion 62 and the radially inner surface of the peripheral wall of the expanded part 64.

As shown also in FIG. 6, the expanded part 64 is formed in a substantially oval tube shape, and the width dimension of the outer peripheral surface in the vertical direction, which is the large diameter direction in FIG. 6, is made larger than the width dimension of the outer peripheral surface in the lateral direction, which is the small diameter direction in FIG. 6. That is, among the wall portions constituting the expanded part 64, the portions constituting the wall portions in the lateral direction in FIG. 6 comprise small-diameter parts 66, 66, while the portions constituting the wall portions in the vertical direction in FIG. 6 comprise large-diameter parts 68, 68. The direction of opposition of the small-diameter parts 66, 66 and the direction of opposition of the large-diameter parts 68, 68 are orthogonal to each other.

The outside diameter dimension of the outer peripheral surface of each of the large-diameter parts 68, 68 gradually increases from the distal end side to the proximal end side, and the outer peripheral surface of the cylindrical portion 62 and the outer peripheral surface of the large-diameter parts 68, 68 are connected by a smooth curved surface. The wall thickness dimension from the cylindrical portion 62 to the large-diameter parts 68, 68 is made substantially constant in the needle axis direction and smaller than the wall thickness dimension of the small-diameter parts 66, 66. With this configuration, in the inside of the expanded part 64, there is formed an internal space 70 on the proximal end side of the inner hole 60 penetrating the needle tip protector 10, and the cross section of the internal space 70 has a substantially elliptical shape in which the vertical dimension in FIG. 6 is larger than the lateral dimension in FIG. 6 and its vertical dimension in FIG. 6 gradually increases toward the proximal end side.

In addition, the large-diameter parts 68, 68 include respective through windows 72, 72 serving as needle hub engagers which penetrate in the plate thickness direction and extend with a predetermined circumferential dimension. The circumferential dimension of the through windows 72, 72 is larger than the circumferential dimension of the hooks 56, 56.

Inside the internal space 70, detent pieces 74, 74 serving as a pair of detents projecting inward are integrally formed with the radially inner surface 65 of the peripheral wall 58. In the inside of the large-diameter parts 68, 68 of the expanded part 64, these detent pieces 74, 74 are provided to positions corresponding to the large-diameter parts 68, 68, that is, the detent pieces 74, 74 are opposed in the vertical direction (spaced apart from each other in the circumferential direction) in FIG. 6.

That is, in the front end portion of the expanded part 64, an annular stepped surface 76 is formed on the radially inner surface 65 of the peripheral wall 58 and extends in the axis-perpendicular direction with a predetermined dimension C (see FIG. 9), with the distal end side of the stepped surface 76 made larger in diameter than the proximal end side. In short, the stepped surface 76 faces forward and extends radially outward. The dimension C in the axis-perpendicular direction of the stepped surface 76 is smaller than the dimension B in the axis-perpendicular direction of the distal-end-side restricting surface 42 of the detaining recess 36. Further on the proximal end side than the stepped surface 76, the detent pieces 74, 74 protrude from the stepped surface 76 toward the proximal end side of the peripheral wall 58. The detent pieces 74, 74 extend from the stepped surface 76 toward the proximal end side in a direction substantially parallel to the needle axis direction and are each curved in the circumferential direction, and protruding distal ends thereof (proximal end in the needle axis direction) are provided with respective detent claws 78, 78 bending toward the radially inner side.

The radially inner surfaces of these detent claws 78, 78 are each curved in the circumferential direction, and the radius of curvature of the radially inner surface of the detent claws 78, 78 is roughly equal to the outer diameter radius of the small-diameter tube part 32 of the needle hub main body 26. The distance between the opposed radially inner surfaces of the detent claws 78, 78 in the diametrical direction is substantially equal to the outside diameter dimension of the small-diameter tube part 32, while being smaller than the maximum outside diameter dimension of the distal end portion of the tapered surface 34. However, the distance between the opposed radially inner surfaces of the detent claws 78, 78 may be slightly smaller or be slightly larger than the outside diameter dimension of the small-diameter tube part 32.

Further, proximal end faces (protruding distal end faces) 79, 79 of the detent claws 78, 78 are configured such that the radially inner sides thereof comprise vertical surfaces 79*a*, 79*a* which extend in the axis-perpendicular direction with a predetermined dimension D (see FIG. 9), while the radially outer sides thereof comprise inclined surfaces 79*b*, 79*b* which incline toward the distal end side as they go to the radially outer side. In the present embodiment, the dimension D in the axis-perpendicular direction of the vertical surfaces 79*a*, 79*a* is substantially the same as or slightly larger than the dimension A in the axis-perpendicular direction of the proximal-end-side restricting surface 40 of the detaining recess 36. With this configuration, as will be described later, when the detent claws 78, 78 come into abutment against the proximal-end-side restricting surface 40 and movement of the needle unit 20 to the distal end side (movement of the needle tip protector 10 to the proximal end side in the needle axis direction) is restricted, the entire surface of the proximal-end-side restricting surface 40 comes into abutment against the vertical surfaces 79*a*, 79*a*, so that a sufficiently large abutting area can be obtained. Furthermore, since the inclined surfaces 79*b*, 79*b* positioned on the radially outer side of the vertical surfaces 79*a*, 79*a* incline toward the distal end side as they go to the radially outer side, the vertical surfaces 79*a*, 79*a* and the proximal-end-side restricting surface 40 are able to come into abutment without being interfered by the inclined surfaces 79*b*, 79*b*, thereby more reliably achieving the effect of preventing relative movement of the needle unit 20 and the needle tip protector 10 in the axial direction.

Further, the protruding distal ends (detent claws 78, 78) of the detent pieces 74, 74 are located further on the distal end side than the proximal end of the expanded part 64. That is, the entirety of the detent pieces 74, 74 are provided in the internal space 70 of the expanded part 64 in a housed state.

In the present embodiment, a wing-like part 80 is provided at the distal end portion of the needle tip protector 10. That is, the distal end portion of the cylindrical portion 62 comprises a small-diameter tubular part 82 having a diameter smaller than that of the other portion, and on the outer circumferential surface of the small-diameter tubular part 82, a plurality of ridges 84 are formed so as to project radially outward. A mating tube part 90 including a pair of wing main bodies 88, 88 is externally fitted onto the small-diameter tubular part 82 via coupling parts 86, 86, and a stopper 92 is externally fitted onto the ridges 84, whereby the wing-like part 80 is attached to the distal end portion of the needle tip protector 10. The wing-like part 80 is formed of, for example, a soft synthetic resin.

The indwelling needle assembly 12 is configured by inserting the needle unit 20 from the proximal end opening of the inner hole 60 of the needle tip protector 10 having the structure as described above. Here, in the state before use of the indwelling needle assembly 12 shown in FIG. 1 and the like, the needle tip 14 of the indwelling needle 16 is located further on the distal side than the needle tip protector 10, and the needle tip 14 is exposed. In such a state, the hooks 56, 56 of the engaging arms 50, 50 provided to the needle hub 22 are inserted and detained with the through windows 72, 72 provided to the expanded part 64 of the needle tip protector 10. By so doing, the needle tip protector 10 and the needle hub 22 (the needle unit 20) are brought into a coupled state, so that the needle tip 14 is held in a protruding state.

In this initial state, the detent claws 78, 78 of the needle tip protector 10 are in abutment against the outer peripheral surface of the small-diameter tube part 32 of the needle hub main body 26. The detent claws 78, 78 may slightly be pressed toward the radially outer side by coming into abutment against the outer peripheral surface of the small-diameter tube part 32, or may be slightly remote from the outer peripheral surface of the small-diameter tube part 32.

The indwelling needle assembly 12 having such a structure is used for infusion, blood collection, and hemodialysis through the fluid flow path 48 by the indwelling needle 16 being stuck into the blood vessel of the patient and placed therein. Since the wing-like part 80 is provided to the indwelling needle assembly 12 of the present embodiment, for example, it is possible to stick the indwelling needle 16 while pinching the wing-like part 80. Further, when placing the indwelling needle 16 in a puncturing state, it is possible to fix the indwelling needle 16 with a wide contact area to the skin by fixing it with a tape at the position of the wing-like part 80.

When removing the indwelling needle 16, the engaging arms 50, 50 of the needle hub 22 are pressed inward with fingers while keeping the needle tip protector 10 fixed by the tape at the wing-like part 80. By so doing, the detainment between the hooks 56, 56 and the through windows 72, 72 is released, and the needle unit 20 can be moved toward the proximal end side with respect to the needle tip protector 10. Furthermore, by moving the needle unit 20 to the proximal end side with respect to the needle tip protector 10 and removing the indwelling needle 16 from the skin, the needle tip protector 10 is moved to the needle tip 14 side of the needle unit 20.

At this time, even if the engaging arms 50, 50 are pressed inward by some external force and the detainment between the needle hub 22 (needle unit 20) and the needle tip protector 10 is unintentionally released, the outer circumferential surface further on the distal end side than the small-diameter tube part 32 to which the detent claws 78, 78 abut comprises the tapered surface 34 whose outside diameter dimension gradually increases toward the distal end side, so that the needle unit 20 is configured not to move unless an external force for moving the needle unit 20 toward the proximal end side with respect to the needle tip protector 10 is applied. By so doing, it is possible to prevent the needle tip 14 of the indwelling needle 16 from being inadvertently protected by the needle tip protector 10.

Here, by moving the needle unit 20 toward the proximal end side with respect to the needle tip protector 10, the detent pieces 74, 74 are pressed to the radially outer side by the tapered surface 34 of the needle hub main body 26 while the detent claws 78, 78 are caused to slide with respect to the tapered surface 34. As a result, an elastic recovery force toward the radially inner side is exerted on the detent pieces 74, 74 as an urging force. Therefore, the pressing force of the detent claws 78, 78 against the tapered surface 34 becomes a resistance, thereby enabling the user to move the needle unit 20 while confirming the feeling that the user withdraws the needle unit 20 with respect to the needle tip protector 10.

Figure 7:
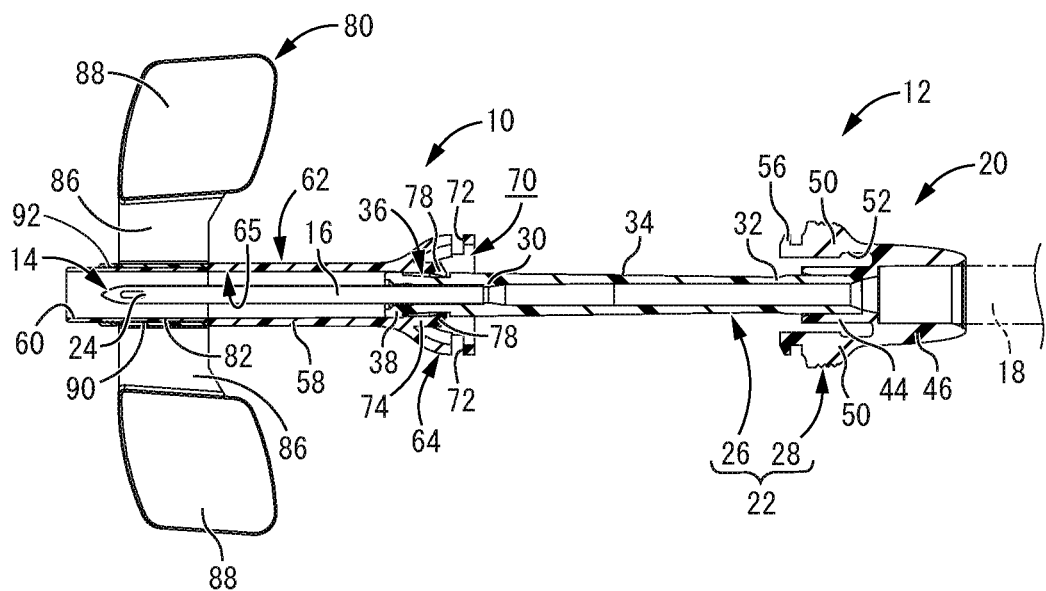
FIG. 7 is a vertical cross sectional view of the indwelling needle assembly shown in FIG. 1 with the needle tip protected, corresponding to FIG. 3.
Figure 8:
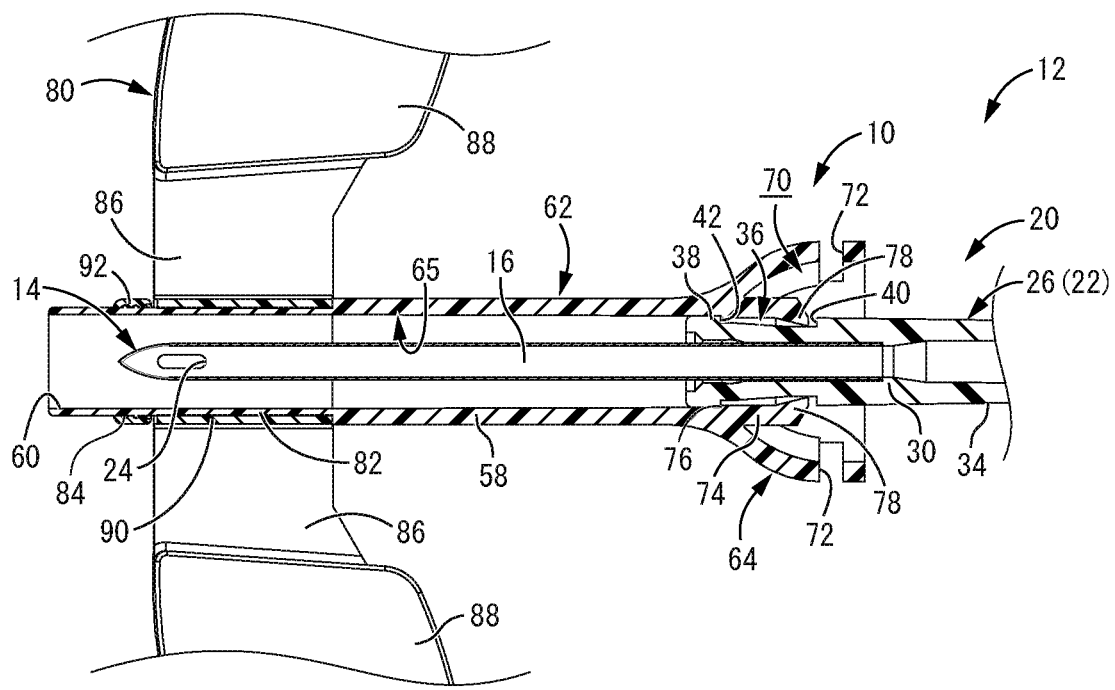
FIG. 8 is an enlarged cross sectional view of a principal part in FIG. 7.

Then, as shown in FIGS. 7 to 9, the needle unit 20 is moved backward relative to the needle tip protector 10 (the needle tip protector 10 is moved forward to the needle tip 14 side of the needle unit 20), whereby the needle tip 14 of the indwelling needle 16 is covered with the needle tip protector 10, as well as the detent claws 78, 78 of the detent pieces 74, 74 climb over the tapered surface 34 of the needle hub main body 26 and elastically recover to enter the detaining recess 36. In this state, the detent claws 78, 78, especially the vertical surfaces 79a, 79a, come into abutment against the proximal-end-side restricting surface 40 of the detaining recess 36 (the detent claws 78, 78 are detained with the proximal-end-side restricting surface 40), so that movement of the needle unit 20 to the distal end side (movement of the needle tip protector 10 to the proximal end side in the needle axis direction) is restricted. This will prevent reexposure of the needle tip 14 of the indwelling needle 16.

At the same time, the stepped surface 76 provided to the front end portion of the detent pieces 74, 74 and the distal-end-side restricting surface 42 of the detaining recess 36 are brought into abutment (the stepped surface 76 is detained with the distal-end-side restricting surface 42), so that the movement of the needle unit 20 to the proximal end side is restricted. This prevents the indwelling needle 16 from being dislodged toward the proximal end side of the needle tip protector 10. Therefore, movement of the needle unit 20 toward both axial sides with respect to the needle tip protector 10 is prevented, and the protected state of the needle tip 14 of the indwelling needle 16 by the needle tip protector 10 is maintained.

That is, in the present embodiment, the detent claws 78, 78 provided on the free end side of the detent pieces 74, 74 serve as the first detents for preventing the needle tip 14 of the indwelling needle 16 from being reexposed. On the other hand, a stepped surface 76 integrally supporting the fixed end sides of the detent pieces 74, 74 serves as a second detent for preventing the needle unit 20 from being dislodged from the proximal end side of the needle tip protector 10. The proximal end faces 79, 79 of the first detents (detent claws 78, 78) have the vertical surfaces 79a, 79a serving as the first axis-perpendicular face extending in the axis-perpendicular direction, while the second detent (stepped surface 76) serves as a second axis-perpendicular face extending in the axis-perpendicular direction. Further, on the inner surface of the detaining recess 36, the proximal end side surface (proximal-end-side restricting surface 40) serves as the third detent as well as a third axis-perpendicular face extending in the axis-perpendicular direction, while the distal end side surface (distal-end-side restricting surface 42) serves as a fourth detent as well as a fourth axis-perpendicular face extending in the axis-perpendicular direction.

In particular, in the present embodiment, since the pair of detents (the detent pieces 74, 74) are provided, in combination with the detents being integrally formed with the peripheral wall 58 of the needle tip protector 10, when the needle tip protector 10 as described above is moved to the distal end side of the indwelling needle 16 and detained by the first detent, a trouble such as rattling of the needle tip protector 10 against the needle unit 20 can be effectively prevented. By providing two, or three or more detents (detent pieces) in this way, the needle tip protector 10 is more reliably prevented from moving backward to the proximal end side of the indwelling needle 16, thereby more stably achieving effect of preventing reexposure of the needle tip. In this case, it is preferable that the plurality of detents are provided substantially symmetrically with respect to the central axis of the needle tip protector 10.

Then, in a state where the needle tip 14 of the indwelling needle 16 is protected by the needle tip protector 10, the tape fixation at the wing-like part 80 is released, and the indwelling needle assembly 12 is detached from the patient. According to this removal procedure, since the needle tip 14 is not exposed at all from the puncture of the indwelling needle 16 to the disposal thereof, erroneous puncture or the like can be more reliably prevented. However, the procedure of protecting the needle tip 14 is not limited to the above procedure, and after releasing the tape fixation at the wing-like part 80 and removing the indwelling needle 16 from the blood vessel, the needle unit 20 may be moved backward with respect to the needle tip protector 10 so as to protect the needle tip 14 of the indwelling needle 16.

When the detent claws 78, 78 have entered the detaining recess 36, the distal ends of the detent claws 78, 78 come into abutment against the bottom surface of the detaining recess 36. By so doing, the impact and sound of the abutment can be confirmed by the user, thereby avoiding the risk of stopping withdrawing the needle unit 20 in the middle of the operation, for example. Accordingly, the needle tip 14 of the indwelling needle 16 can be more reliably protected by the needle tip protector 10.

In the needle tip protector 10 and the indwelling needle assembly 12 having the above-described structure, the detent pieces 74, 74 for preventing the needle tip 14 of the indwelling needle 16 from being reexposed are provided inside the tubular peripheral wall 58, especially in their entireties. Thus, it is substantially impossible to inadvertently contact the detent pieces 74, 74 from the outside. Therefore, with the needle tip 14 of the indwelling needle 16 protected by the needle tip protector 10, it is possible to effectively prevent unintentional release of the detainment between the detent pieces 74, 74 and the detaining recess 36, and consequent reexposure of the needle tip 14 of the indwelling needle 16 from the needle tip protector 10.

In particular, the detent pieces 74, 74 are provided in the expanded part 64 enlarged on the proximal end side of the needle tip protector 10. Accordingly, while sufficiently obtaining the size of the detent pieces 74, 74, for the needle hub 22 (needle hub main body 26) inserted between the detent pieces 74, 74, it is also possible to adopt the one having a sufficiently large outside diameter dimension. Furthermore, in the present embodiment, since the expanded part 64 has a substantially oval shape and its outer peripheral surface smoothly continues from the outer peripheral surface of the cylindrical portion 62, the risk that the expanded part 64 or the like may contact the patient and make the patient feel pain is reduced.

Further, since the detent pieces 74, 74 are provided inside the large-diameter parts 68, 68 constituting the substantially oval-shaped expanded part 64, the inside space of the large-diameter parts 68, 68 can be advantageously utilized, while also avoiding the large-diameter parts 68, 68 becoming thick. This will suppress occurrence of dimensional errors and deterioration of quality precision due to mixing of air bubbles into the member during molding or the like. In addition, it is preferable that the detents (detent pieces 74, 74) are provided so as to extend in the same direction as the large-diameter parts 68, 68 do (to the proximal end side in the axial direction). With such a configuration, it is unnecessary to provide the expanded part 64 larger than necessary, and the inside space of the large-diameter parts 68, 68 can be advantageously utilized, while also avoiding the large-diameter parts 68, 68 becoming thick. This will suppress occurrence of dimensional errors and deterioration of quality precision due to mixing of air bubbles into the member during molding or the like.

Further, by providing the detent pieces 74, 74 so as to protrude into the inside of the peripheral wall 58, when the needle tip protector 10 is manufactured by molding, for example, the molding die can be removed in the needle axis direction of the needle tip protector 10, thereby minimizing the number of types of mold. Therefore, the manufacturing efficiency of the needle tip protector 10 may be improved.

In particular, since the detent pieces 74, 74 extend toward the proximal end side, smooth withdrawal can be realized without catching or the like during withdrawing the needle unit 20 with respect to the needle tip protector 10.

Further, since the pair of detent pieces 74, 74 are provided so as to be opposed to each other in the diametrical direction, with the needle tip 14 of the indwelling needle 16 protected by the needle tip protector 10, namely, with the detent pieces 74 and the detaining recess 36 detained, the needle hub main body 26 can be clamped between the detent pieces 74, 74 in the diametrical direction. Therefore, the needle tip protector 10 and the needle unit 20 (needle hub main body 26) do not wobble in the diametrical direction, and the protected state of the needle tip 14 of the indwelling needle 16 by the needle tip protector 10 may be stably maintained.

Further, with the needle tip 14 protected, by the detent claws 78, 78 that serve as the first detent and the proximal-end-side restricting surface 40 of the detaining recess 36 that serves as the third detent coming into abutment against each other, it is possible to prevent the needle tip protector 10 from moving toward the proximal end side with respect to the needle unit 20. On the other hand, by the stepped surface 76 that serves as the second detent and the distal-end-side restricting surface 42 of the detaining recess 36 that serves as the fourth detent coming into abutment against each other, it is possible to prevent the needle tip protector 10 from moving toward the distal end side with respect to the needle unit 20. Here, since the first to fourth detents have the respective first to fourth axis-perpendicular faces extending in the axis-perpendicular direction, there is no undercut shape and molding is easy, while the abutting force and the abutment reaction force can be efficiently generated as an axial force. In addition, it is possible to sufficiently ensure the respective abutment areas, thereby more reliably preventing the needle tip protector 10 from moving toward the distal end side and the proximal end side with respect to the needle unit 20.

Figure 10:
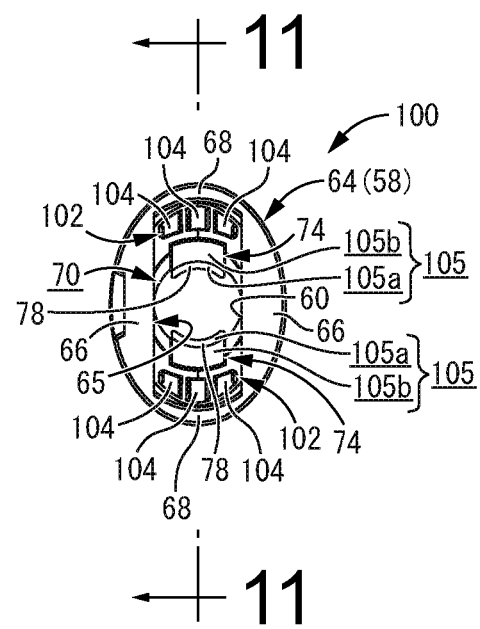
FIG. 10 is a right side view showing a needle tip protector for an indwelling needle according to a second embodiment of the present invention, corresponding to FIG. 6.
Figure 11:
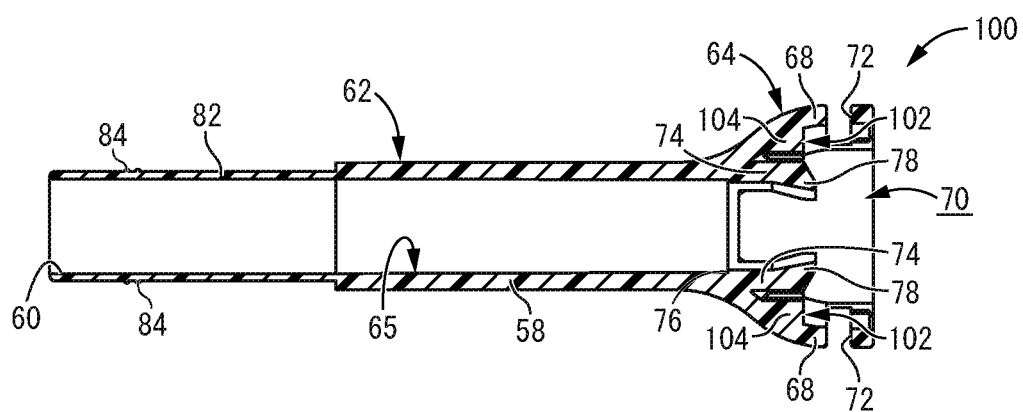
FIG. 11 is a cross sectional view taken along line 11-11 of FIG. 10.

Next, FIGS. 10 and 11 show a needle tip protector 100 for an indwelling needle according to a second embodiment of the present invention. The structure of the needle tip protector 100 of the present embodiment is substantially the same as that of the first embodiment, but in the present embodiment, in the internal space 70 of the expanded part 64 on the proximal end side, provided is a deformation amount limiter 102 for limiting the amount of deformation of the detent pieces 74, 74 serving as the detents to the radially outer side. In the present embodiment, components and parts that are substantially identical with those in the preceding first embodiment will be assigned like symbols and not described in any detail.

Specifically, in the present embodiment, in the internal space 70 of the expanded part 64, the deformation amount limiters 102, 102 are respectively provided between the peripheral wall 58 and the detent pieces 74, 74 in the radial direction. That is, on the radially outer side of the detent pieces 74, 74, the deformation amount limiters 102, 102 projecting toward the proximal end side are integrally formed with the radially inner surface 65 of the large-diameter parts 68, 68 constituting the expanded part 64. In other words, the wall portions constituting the large-diameter parts 68, 68 of the expanded part 64 are partially thickened, so that the deformation amount limiters 102, 102 are formed.

Since the expanded part 64 gradually expands radially outward as it goes toward the proximal end side, the deformation amount limiters 102, 102 gradually increase in radial dimension (vertical dimension in FIG. 11), and in the vertical cross section shown in FIG. 11, each deformation amount limiter 102 is formed in a substantially right triangle shape. The radially inner surfaces of the deformation amount limiters 102, 102 extend substantially in parallel with the detent pieces 74, 74 (that is, substantially parallel to the needle axis direction of the indwelling needle 16), while the proximal end surfaces thereof extend in a direction substantially orthogonal to the needle axis direction of the indwelling needle 16. The proximal end surfaces of the deformation amount limiters 102, 102 are located further on the distal end side in the needle axis direction than the proximal end in the needle axis direction (protruding distal end) of the detent pieces 74, 74, and the deformation amount limiters 102, 102 are entirely housed in the internal space 70 of the expanded part 64.

Particularly, in the present embodiment, each of the deformation amount limiters 102, 102 is constituted by three protrusions 104, 104, 104 projecting from the radially inner surface 65 of the expanded part 64 toward the proximal end side. These three protrusions 104, 104, 104 are disposed between the wall portions constituting the small-diameter parts 66, 66 (between the left and right sides in FIG. 10) which are made thicker than the large-diameter parts 68, 68, and are spaced apart from one another.

In addition, these three protrusions 104, 104, 104 are also spaced apart from the detent piece 74 in the radial direction (vertical direction in FIG. 10) by an appropriate distance so as not to hinder the movement of the needle tip protector 100 from the state before needle tip protection (see FIGS. 3 and 4, for example) to the state in which the needle tip is protected (see FIGS. 7 and 8, for example). The radially inner surface of the deformation amount limiter 102 including these three protrusions 104, 104, 104 has a curved shape substantially corresponding to the outer peripheral surface of the detent piece 74, and the three protrusions 104, 104, 104 and the detent piece 74 are remote from each other by a substantially constant distance. Here, the remote distance between the protrusions 104, 104, 104 and the detent piece 74 is set to a size so as not to inhibit deformation of the detent piece 74 toward the radially outer side during movement of the needle tip protector 100 toward the distal end side with respect to the needle unit 20, as well as to such a size that the amount of deformation of the detent piece 74 is restricted by abutting against the deformation amount limiter 102 (protrusions 104, 104, 104) at the time of bending deformation of an indwelling needle assembly 106 as will be described later.

Further, in the present embodiment, in proximal end faces 105, 105 of the detent pieces 74, 74, the dimension E (see FIG. 13) in the axis-perpendicular direction of vertical surfaces 105a, 105a serving as the first axis-perpendicular face is smaller than the dimension A in the axis-perpendicular direction of the proximal-end-side restricting surface 40 (third axis-perpendicular face) of the detaining recess 36.

With this configuration, the end a on the radially outer side of the vertical surface 105a of the detent piece 74 is positioned on the radially inner side than the end 13 on the radially outer side of the proximal-end-side restricting surface 40 of the detaining recess 36, so that the end a on the radially outer side of the vertical surface 105a of the detent piece 74 is configured to abut against the proximal-end-side restricting surface 40. In the proximal end faces 105, 105, inclined surfaces 105b, 105b positioned on the radially outer side of the vertical surfaces 105a, 105a incline to the distal end side as they go toward the radially outer side, as in the preceding first embodiment.

Figure 12:
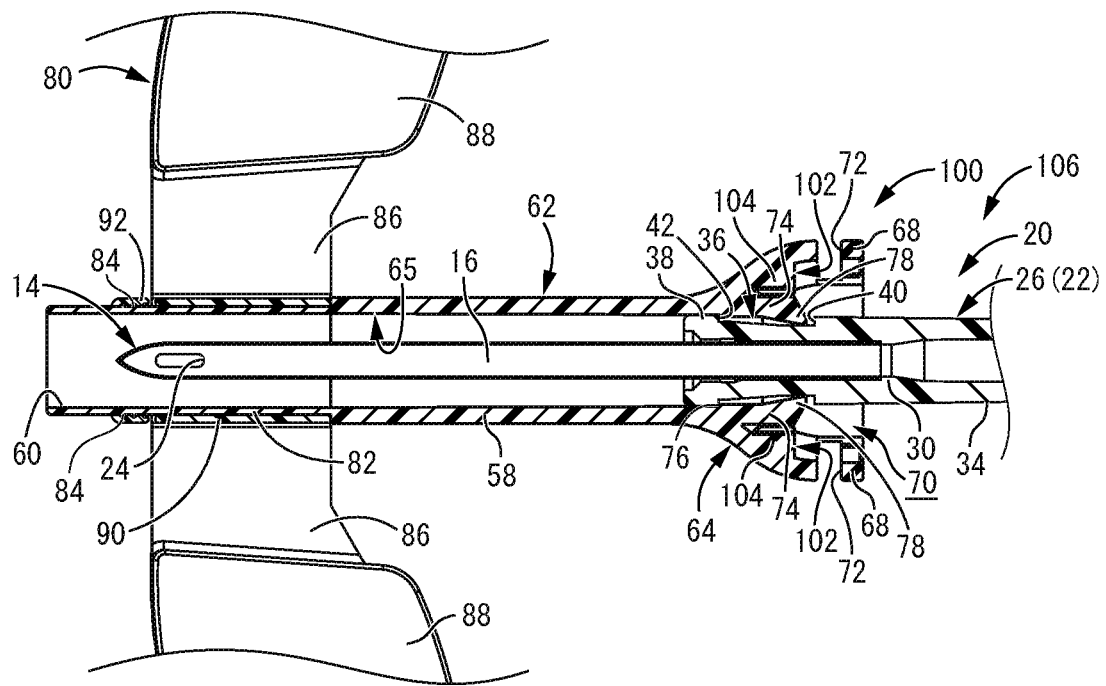
FIG. 12 is a vertical cross sectional view of a principal part of the indwelling needle assembly including the needle tip protector for an indwelling needle shown in FIG. 10 with a needle tip protected, corresponding to FIG. 8.
Figure 13:
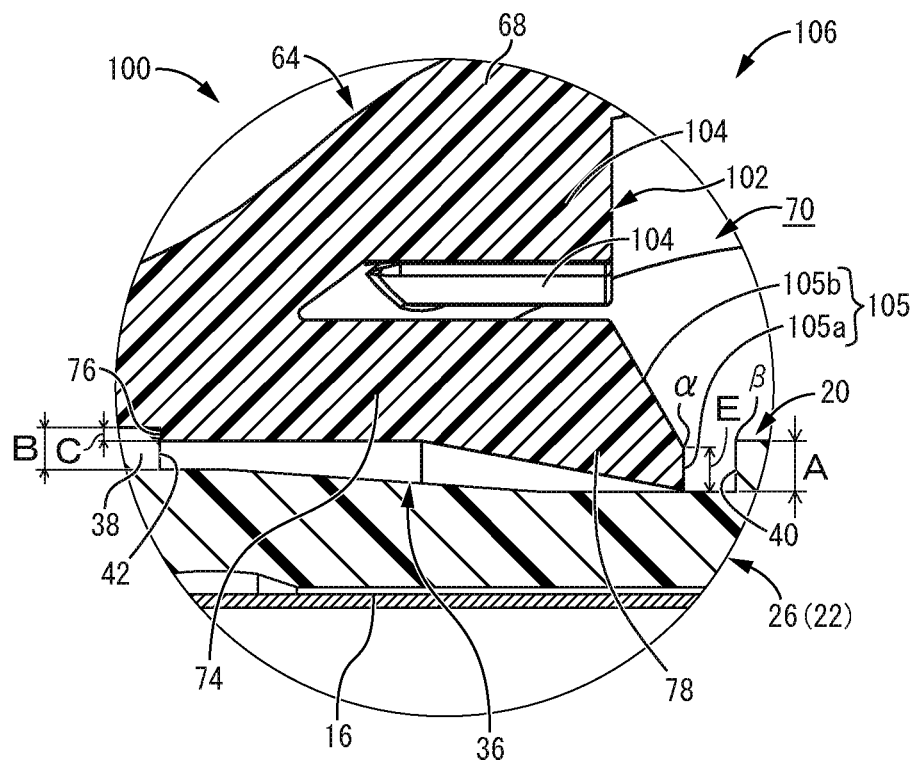
FIG. 13 is an enlarged cross sectional view of a principal part in FIG. 12, corresponding to FIG. 9.

The needle tip protector 100 for an indwelling needle having such a structure is externally mounted about the needle unit 20 having the same structure as that of the first embodiment, whereby an indwelling needle assembly 106 of the present embodiment (see FIG. 12) is constituted. Then, as in the first embodiment, after sticking the indwelling needle assembly 106, as shown in FIGS. 12 and 13, the needle tip protector 100 is moved to the needle tip 14 side of the indwelling needle 16, so that the needle tip 14 of the indwelling needle 16 is protected by the needle tip protector 100. That is, the detent claws 78, 78 provided to the distal ends of the detent pieces 74, 74 enter the detaining recesses 36 provided to the distal end portion of the needle hub main body 26 and are detained therewith, and by the detent claws 78, 78 and the proximal-end-side restricting surface 40 abutting against each other, movement of the needle unit 20 toward the distal end side with respect to the needle tip protector 100 is restricted. Besides, by the stepped surface 76 and the distal-end-side restricting surface 42 abutting against each other, movement of the needle unit 20 toward the proximal end side with respect to the needle tip protector 100 is restricted.

Here, in the present embodiment, since the deformation amount limiters 102, 102 are provided on the radially outer side of the detent pieces 74, 74, in the protected state of the needle tip 14 of the indwelling needle 16, unintentional detachment of the detent claw 78 from the detaining recess 36 can be effectively prevented. Specifically, for example, in the protected state of the needle tip 14, when an external force in the bending direction is exerted on the entireties of the needle tip protector 100 and the needle unit 20, and one detent piece 74 is pushed by the needle hub main body 26 so as to largely deform outward, it is difficult to completely deny the possibility that the detent claw 78 of the other detent piece 74 is lifted outward from the proximal-end-side restricting surface 40 and the detained state is released or the detent piece 74 is damaged etc., resulting in reexposure of the needle tip. Here, in the present embodiment, since the deformation amount of the detent piece 74 to the outside is restricted by the abutment against the deformation amount limiter 102, even when an excessive bending force acts, such unexpected reexposure of the needle tip can be effectively prevented.

Further, the same effect as in the first embodiment can be exhibited also with the needle tip protector 100 for an indwelling needle and the indwelling needle assembly 106 of the present embodiment.

In particular, in the present embodiment, the deformation amount limiters 102, 102 are provided on the radially inner side of the large-diameter parts 68, 68 of the expanded part 64. By appropriately utilizing the internal space 70 of the expanded part 64, it is also possible to avoid increase in size of the needle tip protector 100 and the like due to providing the deformation amount limiting mechanism of the detent pieces 74, 74.

In the present embodiment, the dimension E in the axis-perpendicular direction of the vertical surfaces 105a, 105a of the proximal end faces 105, 105 of the detent pieces 74, 74 is smaller than the dimension A in the axis-perpendicular direction of the proximal-end-side restricting surface 40 of the detaining recess 36, so that the end a on the radially outer side of the vertical surface 105a of the detent piece 74 is configured to abut against the proximal-end-side restricting surface 40. By so doing, for example, when the needle tip protector 100 is to be forcibly moved toward the proximal end side with an excessive force from the state before needle tip protection, it will be effectively prevented that the detent piece 74 is deformed so as to make the detent claw 78 ride over the proximal-end-side restricting surface 40 of the detaining recess 36 and result in release of the detainment. That is, since the vertical surface 105a of the detent claw 78 that abuts against the proximal-end-side restricting surface 40 is deviated toward the radially inner side from the central axis of the detent piece 74, the action of the bending moment due to the abutment reaction force may pose a risk that the detent piece 74 is deformed into a curved shape that is convex outward and the vertical surface 105a of the detent claw 78 is inclined. In the inclined state of the vertical surface 105a, when the end a of the vertical surface 105a is positioned further on the radially outer side than the end 13 of the proximal-end-side restricting surface 40, there is a risk that by the end 13 of the proximal-end-side restricting surface 40 abutting against the inclined vertical surface 105a, a component force in a direction in which the detent claw 78 rides over the proximal-end-side restricting surface 40 may be generated, resulting in unintentional release of the detained state. On the other hand, in the present embodiment, even when the vertical surface 105a of the detent claw 78 is inclined, the abutment of the proximal-end-side restricting surface 40 with respect to the inclined vertical surface 105a is avoided and by the end a of the vertical surface 105a abutting against the proximal-end-side restricting surface 40, it is possible to stably achieve an effective detaining force while avoiding the generation of the component force in the direction of overriding.

Although the embodiments of the present invention have been described above, the present invention is not limitedly interpreted based on the specific description in the embodiment, but may be embodied with various changes, modifications and improvements which may occur to those skilled in the art.

For example, in the preceding embodiments, the detent pieces 74, 74 extend toward the proximal end side, but they may extend toward the distal end side. Also, in the preceding embodiments, the entire detent pieces 74, 74 are housed in the inside of the peripheral wall 58. However, for example, the distal end of the detent may be located outward from the end portion in the needle axis direction of the peripheral wall. In addition, it is not necessary for the substantive detaining portion of the detent (for example, the detent claws 78, 78 in the preceding embodiment) to be provided at the distal end of the detent.

Furthermore, in the preceding embodiments, the radially inner sides of the proximal end faces 79, 79 (105, 105) of the detent pieces 74, 74 serve as the vertical surfaces 79a, 79a (105a, 105a), while the radially outer sides thereof serve as the inclined surfaces 79b, 79b (105b, 105b), but the present invention is not limited to such a mode. Specifically, the proximal end faces 79, 79 (105, 105) of the detent pieces 74, 74 may extend in the axis-perpendicular direction over substantially their entire surfaces without having the inclined surfaces 79b, 79b (105b, 105b), or may alternatively extend in a direction inclined with respect to the axial direction over substantially their entire surfaces without having the vertical surfaces 79a, 79a (105a, 105a). The inclined surfaces 79b, 79b (105b, 105b) may be inclined to the distal end side as they go toward the radially outer side as in the preceding embodiments, or as long they do not interfere with the abutment of the vertical surfaces 79a, 79a (105a, 105a) and the proximal-end-side restricting surface 40, they may be inclined to the proximal end side as they go toward the radially outer side. In addition, with respect to the radially inner side portion of the proximal end faces 79, 79 (105, 105) of the detent pieces 74, 74 and the proximal-end-side restricting surface 40 of the needle hub main body 26, the vertical faces as exemplified may be replaced by inclined surfaces inclined toward the distal end side as they go toward the radially outer side. By so doing, whereas the proximal-end-side restricting surface 40 becomes the undercut having the overhang shape, it is also possible to obtain a larger movement restricting force.

Furthermore, in the preceding embodiments, the pair of detent pieces 74, 74 are provided so as to be opposed to each other in the diametrical direction, but it would also be acceptable to provide a single detent piece 74, or three or more detent pieces 74. In this case, it is preferable that three or more detents are provided at substantially equal intervals in the circumferential direction. Alternatively, the detent may have a substantially tubular shape extending continuously over the entire circumference. Even when two, or three or more detents are provided, it is not necessary that they are opposed in the diametrical direction or provided at equal intervals in the circumferential direction. In addition, the detaining recess provided in the needle hub main body need not be provided continuously over the entire circumference, but it would be acceptable as long as the detaining recess is provided at a position corresponding to the detent in the circumferential direction.

Furthermore, in the preceding embodiments, the stepped surface 76 provided on the fixed end side of the detent pieces 74, 74 of the needle tip protectors 10, 100 and the distal-end-side restricting surface 42 provided on the needle hub 22 (needle hub main body 26) are brought into abutment against each other so as to prevent the needle unit 20 from being dislodged from the proximal end side of the needle tip protector 10, 100, but the dislodgment prevention mechanism of the needle unit is not limited to such a mode. That is, the stepped surface 76 and the distal-end-side restricting surface 42 are not indispensable, and a mechanism for preventing dislodgment of the needle unit may be provided separately from these members.

In the preceding embodiments, the stepped surface 76, the proximal-end-side restricting surface 40, the distal-end-side restricting surface 42, and the like extend in the axis-perpendicular direction. However, they may extend so as to incline with respect to the axis-perpendicular direction.

Further, in the preceding embodiments, the distal end side of the needle tip protector 10, 100 comprises a cylindrical portion 62 having an annular cross section, while the proximal end side thereof comprises an oval tubular expanded part 64, but they are not limited to such shapes. Specifically, various shapes such as a circular shape (including an oval, an ellipse, a semicircle, etc.) and a polygonal shape can be adopted as each of the cross-sectional shapes of the distal end side and the expansion part at the proximal end side of the needle tip protector. However, the expansion part provided on the proximal end side of the needle tip protector is not indispensable, and the needle tip protector may have a mere straight tubular shape.

Furthermore, the shape of the needle unit is not limited. For example, in the preceding embodiments, the needle hub 22 and the needle tip protector 10, 100 are coupled, namely, the hooks 56, 56 are detained with the through windows 72, 72 to maintain the indwelling needle 16 in the exposed state, but the present invention is not limited to such a mode. Specifically, the needle hub engager is not required to have a shape of the through window as in the preceding embodiments, but may have a bottomed groove shape that opens to the radially inner side or the like. Alternatively, a hook serving as a needle hub engager may be formed on the needle tip protector, and a through window, a bottomed groove, or the like may be formed in the needle hub. However, these hooks, through windows, etc. are not indispensable, and in short, the coupling mechanism between the needle hub and the needle tip protector before use is not indispensable.

Further, in the preceding embodiment, the wing-like part 80 is attached to the needle tip protectors 10, 100, but the wing-like part is not indispensable.

Moreover, in the preceding second embodiment, the deformation amount limiters 102, 102 are formed integrally with the expanded part 64 of the needle tip protector 100, but they may be separately formed to be attached later. By so doing, for example, it is possible to form the deformation amount limiter with a material different from that of the needle tip protector.

Furthermore, in the preceding second embodiment, the deformation amount limiters 102, 102 are provided on the radially inner surface 65 of the wall portion constituting the large-diameter parts 68, 68 of the expanded part 64, but the formation position of the deformation amount limiter is not limited at all. That is, the deformation amount limiter may be provided so as to protrude from the radially inner surface of the wall portion constituting the small-diameter part of the expanded part toward the radially outer side of the detents (detent pieces 74, 74), for example. However, the deformation amount limiter is not limited to the mode of being provided on the radially inner surface of the expanded part. For example, the deformation amount limiter may be provided on the outer peripheral surface of the detent, and when the detent elastically deforms toward the radially outer side, the deformation may be restricted by the deformation amount limiter abutting against the radially inner surface of the expanded part.

Further, the shape of the deformation amount limiter is not limited at all, either. In the preceding second embodiment, the deformation amount limiters 102, 102 have a vertical cross section of substantially right triangle shape. However, for example, the deformation amount limiter may have a shape of a projecting piece projecting from the radially inner surface of the expanded part toward the proximal end side or the radially inner side, or may have a shape of a projecting piece projecting from the outer circumferential surface of the detent (detent pieces 74, 74) toward the radially outer side. Furthermore, in the preceding second embodiment, each of the deformation amount limiters 102, 102 is composed of three protrusions 104, 104, 104, but the present invention is not limited to such a mode, and the deformation amount limiter may be composed of one, two, four or more protrusions. By configuring the deformation amount limiters 102, 102 with a plurality of protrusions in this manner, suppression of sink marks (deformation due to thermal shrinkage) after molding and reduction in molding time owing to an improvement in cooling efficiency may be achieved. Particularly, as in the preceding second embodiment, by constituting each of the deformation amount limiters 102, 102 with three protrusions 104, 104, 104, the above effect is stably exhibited, and in addition, it would also be avoidable that the shape of the mold becomes too complicated.

Furthermore, in the preceding second embodiment, the two detent pieces 74, 74 are provided and the deformation amount limiters 102, 102 are provided on the radially outer sides of the respective detent pieces 74, 74. However, the deformation amount limiter may be provided on the radially outer side of only either one of the detents (detent piece 74). Besides, in the case where two or more detents are provided, it is preferable to provide the deformation amount limiter on the radially outer side of each detent, but it is acceptable as long as the deformation amount limiter is provided on the radially outer side of at least one detent.

KEYS TO SYMBOLS

10, 100: needle tip protector for an indwelling needle, 12, 106: indwelling needle assembly, 14: needle tip, 16: indwelling needle, 22: needle hub, 40: proximal-end-side restricting surface (third detent, third axis-perpendicular face), 42: distal-end-side restricting surface (fourth detent, fourth axis-perpendicular face) 58: peripheral wall, 64: expanded part (expansion part), 66: small-diameter part, 68: large-diameter part, 72: through window (needle hub engager), 74: detent piece (detent), 76: stepped surface (second detent, second axis-perpendicular face), 78: detent claw (first detent), 79, 105: proximal end face, 79a, 105a: vertical surface (first axis-perpendicular face), 102: deformation amount limiter

The invention claimed is:

1. A needle tip protector for an indwelling needle configured to cover a needle tip of the indwelling needle by being externally mounted about a needle hub of the indwelling needle and by being moved to a needle tip side of the indwelling needle, the needle tip protector comprising:
   a tubular peripheral wall; and
   at least one detent formed on an inside of the tubular peripheral wall and configured to be detained with the needle hub at a position in a movement of the protector to the needle tip side of the indwelling needle and to prevent backward movement of the protector to a proximal end side of the indwelling needle such that reexposure of the needle tip is prevented, the at least one detent being integrally molded with the tubular peripheral wall;
   wherein the at least one detent comprises a first detent configured to be detained with the needle hub inside the tubular peripheral wall such that reexposure of the needle tip due to movement of the indwelling needle to the needle tip side in the tubular peripheral wall is prevented, and a second detent configured to be detained with the needle hub inside the tubular peripheral wall such that needle dislodgment due to movement of the indwelling needle to the proximal end side of the indwelling needle is prevented.

2. The needle tip protector according to claim 1, wherein the first detent extends within the tubular peripheral wall toward a proximal end side of the peripheral wall.

3. The needle tip protector according to claim 1, wherein the at least one detent is entirely housed inside the tubular peripheral wall.

4. The needle tip protector according to claim 1, wherein the at least one detent comprises a plurality of detents that are remote from each other in a circumferential direction of the tubular peripheral wall.

5. The needle tip protector according to claim 1, further comprising a deformation amount limiter configured to limit an amount of deformation of the at least one detent to a radially outer side.

6. The indwelling needle assembly according to claim 1, wherein the first and second detents are configured to be detained within a detaining recess in the needle hub.

7. The needle tip protector according to claim 1, wherein an expansion part expanding radially outward is provided to a proximal end side of the tubular peripheral wall, and the at least one detent is provided in the expansion part.

8. The needle tip protector according to claim 7, wherein a stepped surface is provided to a front end portion of the expansion part, the stepped surface facing forward and extending radially outward on a radially inner surface of the tubular peripheral wall, and the first detent protrudes backward from a more backward end portion of the expansion part than the stepped surface.

9. The needle tip protector according to claim 7, wherein
   the expansion part has a roughly oval tube shape including a small-diameter part and a large-diameter part that are orthogonal to each other,
   the at least one detent is provided inside the large-diameter part of the tubular peripheral wall, and
   the large-diameter part of the tubular peripheral wall includes a needle hub engager configured to receive the needle hub such that the needle tip of the indwelling needle is held in a protruding state.

10. An indwelling needle assembly comprising:
    the needle tip protector according to claim 1; and
    an indwelling needle having a needle hub at the proximal end side thereof, the indwelling needle being inserted in the needle tip protector such that the indwelling needle is movable in an axial direction, wherein
    the detent provided to the needle tip protector is configured to be detained with the needle hub at a predetermined position where the protector is moved to the needle tip side of the indwelling needle such that reexposure of the needle tip of the indwelling needle is prevented.

11. The indwelling needle assembly according to claim 10, wherein
    the first detent is configured to be detained with a third detent provided on an outer circumferential surface of the needle hub such that reexposure of the needle tip due to movement of the indwelling needle to the needle tip side in the tubular peripheral wall is prevented,
    a proximal end face of the first detent includes a first axis-perpendicular face that crosses orthogonally to a needle axis direction of the indwelling needle, and
    the third detent includes a third axis-perpendicular face that crosses orthogonally to the needle axis direction of the indwelling needle.

12. The indwelling needle assembly according to claim 11, wherein the first-axis perpendicular face is positioned on an inner side of an expansion part of the tubular peripheral wall and the third-axis perpendicular face is provided on an outer surface of the needle hub.

13. The indwelling needle assembly according to claim 10, wherein
    the needle hub includes a detaining recess, and an inner surface on a proximal end side of the detaining recess comprises a third detent with which the first detent is configured to be detained.

14. The indwelling needle assembly according to claim 13, wherein the first and second detents are configured to be detained within the detaining recess in the needle hub.

15. The indwelling needle assembly according to claim 14, wherein the detaining recess in the needle hub is configured to be contained within the tubular peripheral wall when the needle tip is disposed within the needle tip protector.

\* \* \* \* \*